United States Patent [19]

Solomon

[11] 4,253,451

[45] Mar. 3, 1981

[54] SURGICAL DRAPE

[76] Inventor: Alan Solomon, 16 Fox Run Rd., Dover, Mass. 02030

[21] Appl. No.: 78,043

[22] Filed: Sep. 24, 1979

[51] Int. Cl.$^3$ ............................................. A61F 13/00
[52] U.S. Cl. ................................................ 128/132 D
[58] Field of Search .................................... 128/132 D

[56] References Cited

U.S. PATENT DOCUMENTS

| | | | |
|---|---|---|---|
| 2,593,121 | 4/1952 | Djorup | 128/132 D |
| 2,715,902 | 8/1955 | Shaffer et al. | 128/132 D |
| 3,251,360 | 5/1966 | Melges | 128/132 D |
| 3,856,006 | 12/1974 | Krzewinski | 128/132 D |
| 3,889,667 | 6/1975 | Collins | 128/132 D |
| 3,955,569 | 5/1976 | Krzewinski et al. | 128/132 D |
| 4,027,665 | 6/1977 | Scrivens | 128/132 D |

*Primary Examiner*—Lawrence W. Trapp
*Attorney, Agent, or Firm*—Morse, Altman, Oates & Dacey

[57] ABSTRACT

A surgical drape for use in hip or knee surgery designed to provide a substantially complete seal around an operative site in a one step application and having two main sections integrally connected along a main folding line, with one main section being continuous along the main folding line and the second main section being trifurcated into a median flap connected to the main folding line along a narrow junction and a pair of side flaps connected to the main folding line along wide junctions. The median flap extends substantially equidistantly from the main folding line as the continuous main section extends therefrom in the opposite direction, while the pair of side flaps extend from the main folding line about midway of the median flap. The median flap is provided about its periphery with a strip of surgical adhesive and the pair of side flaps have a strip of surgical adhesive about their edges adjacent the median flap. The trifurcated main section is folded onto the first main continuous section and so folded is positioned, with the median flap under a limb of a patient so that its narrow connecting junction is adjacent the edge of the operative site. Then the median flap and the pair of side flaps are wrapped about the limb so as to provide a substantially complete seal around the operative site with the median flap surrounding one part and the pair of side flaps surrounding the remaining part of the operative site, which site is the only part of the limb left exposed.

5 Claims, 4 Drawing Figures

SURGICAL DRAPE

BACKGROUND OF THE INVENTION

1. Field of the Invention

The present invention relates to a surgical drape provided with a free leg drape and particularly adapted for use in highly complex surgical procedure invloving the hip or the knee. In particular, it is directed to such a surgical drape designed to provide a substantially complete seal around the operative site in a one-step application that avoids contamination and requires no clips for securing it to the limb. The invention is particularly concerned with the provision of a surgical drape of unique construction, providing a free drape in one of its main sections which, together with a pair of side flaps, is designed completely to seal around the surgical site so that only the surgical site is left exposed.

2. Description of the Prior Art

The preparation of a patient for hip or knee surgery involves covering all exposed portions of the patient except the area of the incision, i.e., the surgical site. Heretofore known surgical drapes have provided what is called a fenestration through which the particular surgical site, such as a limb or the hip of the patient, extends. U.S. Pat. No. 3,926,185 of Krzewinski, issued on Dec. 16, 1975, shows a surgical drape having a slit that merges into an enlarged fenestration through which the limb of a patient protrudes, the entire limb being exposed on top of the drape. U.S. Pat. No. 3,930,497 of Krebs et al., issued on Jan. 6, 1976, shows a drape with generally U-shaped fenestration through which the patient's limb extends. In both of these instances, in order to avoid contamination, the surgeon will have to provide complete coverage for the exposed portion of the limb by means of a stockinette which will have to be pulled over the limb and making sure that it stops short of the operative site.

SUMMARY OF THE INVENTION

It is therefore a principal object of the present invention to eliminate these drawbacks of prior art surgical drapes as discussed above by providing an improved surgical drape of unique construction that substantially seals completely around the operative site of a patient in a one-step application so as to avoid unnecessary further work and possible contamination. More particularly, it is an object of the present invention to provide a surgical drape for use in highly complex surgical procedures such as involving a hip or knee. It is a further object of the present invention to provide an improved surgical drape that requires no clips for securing it to a limb of a patient and that in a one-step application substantially completely envelops the surgical site so that only the site for the surgical incision remains exposed.

In accordance with the present invention, there is provided an improved surgical drape of the disposable kind that can be used in highly complex surgical procedures without the drawbacks of surgical drapes heretofore known. The surgical drape of the present invention simplifies the wrapping procedure, saves valuable time, reduces cost, avoids contamination and provides a drape that can completely seal around the operative site in a one-step application.

The surgical drape of the present invention comprises two main sections integrally connected along a main folding line, with one main section being continuous along the main folding line and with a second main section being trifurcated into a median flap, which may otherwise be characterized as being a free leg drape, and a pair of side flaps. The median flap is connected to the main folding line along a narrow junction while the pair of side flaps are connected to the main folding line along wide junctions. The median flap is provided about its periphery with a strip of surgical adhesive and the pair of side flaps are each provided with a strip of surgical adhesive about their edges adjacent the median flap. As is known, the surgical adhesive may be protected prior to use by suitable release sheets. The median flap extends substantially equidistantly from the main folding line as the continuous main section extends therefrom in the opposite direction, while the pair of side flaps extend from the main folding line about midway of the median flap. Prior to use, the trifurcated main section is first folded onto the first main section and then the surgical drape of the invention is ready for use by positioning its median flap under a patient's limb so that its narrow connecting junction is underneath and adjacent the edge of the operative site. The median flap and the pair of side flaps are then simply and quickly wrapped about the limb of the patient so as to provide a substantially complete seal around the site of incision, completely enveloping all other areas of limb and leaving but the surgical site exposed. There is thus no need for using a stockinette or other drapes. Preferably, the surgical drape of the invention is made of a non-woven fabric or a wet formed non-woven containing long fibers and the drape is cut from a sheet made of such non-woven fabric formed into a two-ply bonded fiber material that has been rendered nonabsorbent.

Other objects of the present invention will in part be obvious and will in part appear hereinafter.

The invention accordingly comprises the products, together with their parts, elements and interrelationships, that are exemplified in the following disclosure, the scope of which will be indicated in the appended claims.

BRIEF DESCRIPTION OF THE DRAWINGS

A fuller understanding of the nature and objects of the present invention will become apparent upon consideration of the following detailed description taken in connection with the accompanying drawings, wherein.

DETAILED DESCRIPTION OF THE PREFERRED EMBODIMENT

While the invention will be described in connection with a preferred embodiment, it will be understood that it is not intended to limit the invention to this embodiment. On the contrary, the invention is intended to cover all alternatives, modifications and equivalents as may be included within the spirit and scope of the invention as defined by the appended claims.

Figure 1:
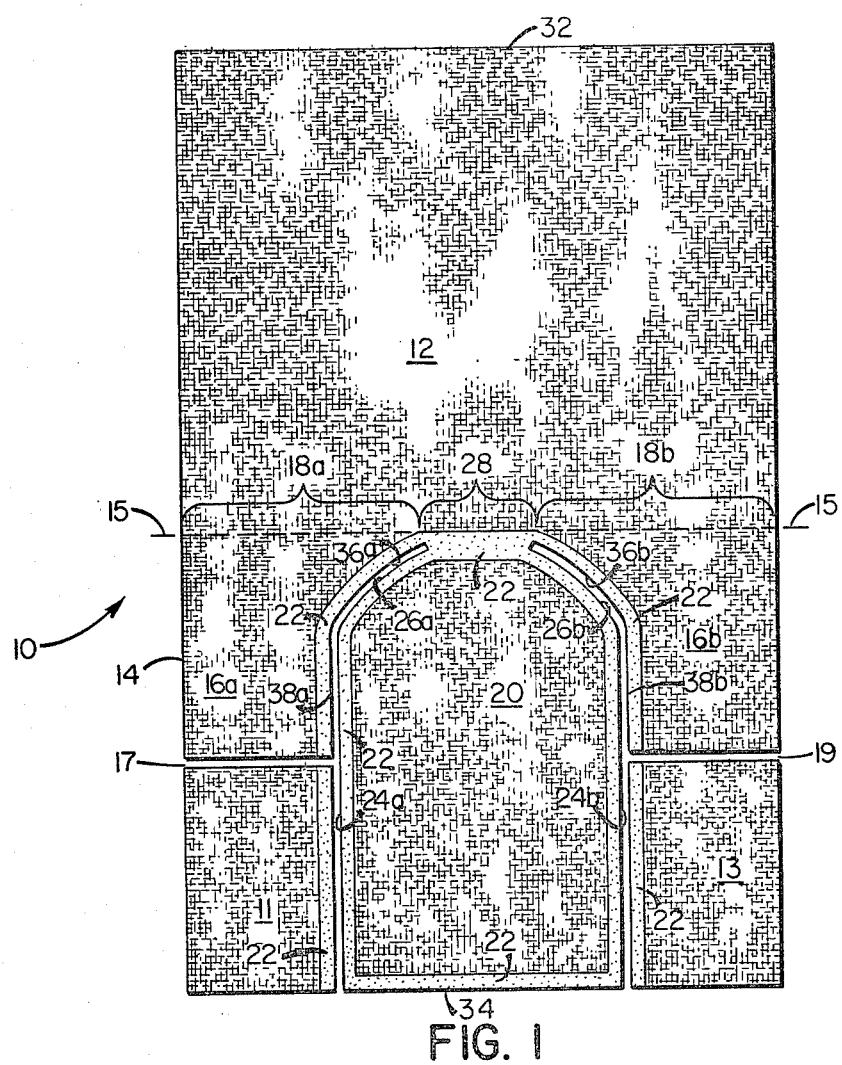
FIG. 1 is a plan view of the surgical drape of the present invention showing the same after it has been cut from a sheet made from a two-ply bonded fiber nonabsorbent material, and showing its unique features embodying the present invention.

Referring particularly to FIG. 1 which depicts one embodiment of the present invention, a surgical drape 10 having a substantially rectangular shape is preferably cut from a sheet of two-ply bonded fiber nonabsorbent material. Preferably, the material is a drapable nonwoven fabric such as a scrim reinforced tissue or a wet-formed non-woven fabric containing long fibers. The material may for instance be a scrim reinforced tissue product available under the trademark KAYCEL from the Kimberly Clark Corporation Of Neenah, Wis. or may be made from wood pulp with a nylon scrim bonded double layer, or from a wood fiber polyester and rayon which is nonabsorbable and treated with a flame retardant, or may be a Tyvec spun bonded olefin, or a Johnson & Johnson spun-laced nonabsorbent, flame retardant polyester and rayon. Such relatively non-linting liquid repellent materials considerably reduce the risk to the patient as by avoiding contamination for the most part. The drape once cut and formed is, of course, sterilized so that it is in a sterilized condition before use, all as well understood in the art.

The surgical drape 10 of the invention as shown in FIG. 1 in plan view has just been cut from such a nonwoven material and is shown as comprising essentially a first main continuous section 12 and a second main section 14 that is trifurcated. The first main section 12 is continuous along a main folding line 15 while the second main section 14 is trifurcated into a median flap 20 that is connected to the first main section 12 at the main folding line 15 along a narrow junction 28, while a pair of side flaps 16a and 16b are shown connected to the first main section 12 along wide junctions 18a and 18b, respectively.

The median flap 20 is formed with a pair of arcuate shoulders 26a and 26b adjacent the narrow connecting junction 28. These arcuate shoulders 26a and 26b then proceed into straight parallel cuts 24a and 24b, respectively, terminating in a distal end 34 which is parallel to and spaced equidistantly from a distal end 32 of the first main continuous section 12 as measured from the main folding line 15. In similar fashion, the pair of side flaps 16a and 16b are formed with a pair of arcuate segments 36a and 36b commencing from the narrow junction 28, which arcuate segments closely parallel the arcuate shoulders 26a and 26b of the median flap 20. Also, these arcuate segments then proceed to straight cuts 38a and 38b respectively, which again parallel the straight cuts 24a and 24b of the median flap. The side flaps 16a and 16b are then cut by cuts 17 and 19 substantially midway down the length of the median flap 20 measured from the main folding line 15 so as to form portions 11 and 13 on each side of the median flap, which portions 11 and 13 may conveniently be used as marking towels as hereinafter more fully described. Before the cutting operation is effected, a strip 22 of surgical adhesive, preferably with a release tape, preferably is deposited in a one-step application on the surgical drape 10 of the invention so as to completely surround the periphery of the median flap 20, including its narrow connecting junction 28, as well as on the side flaps 16a and 16b, including its arcuate segments 36a and 36b and straight cuts 38a and 38b. In the same application, a strip 22 of surgical adhesive also is applied to the portions 11 and 13 in the vicinity adjacent the straight cuts 24a and 24b of the median flap, substantially as shown. Following the application of such a strip 22 of surgical adhesive in the areas just described and shown in FIG. 1, the sheet material can then be presented to a suitable cutting machine so as to cut the drape 10 into the configuration shown.

Figure 2:
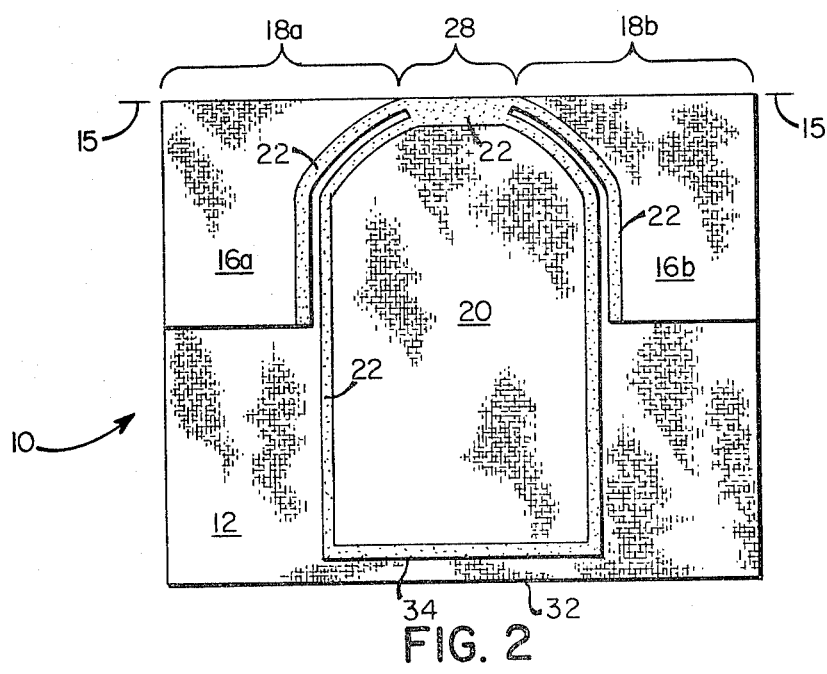
FIG. 2 is a plan view of the surgical drape of FIG. 1 after its trifurcated main section has been folded onto its continuous main section along a main folding line.

Before the surgical drape of the invention as described in and with reference to FIG. 1 is ready for use, two tasks have to be accomplished. The first is its sterilization and the second is its folding along its main folding line 15, substantially as shown in FIG. 2. As may be noted therefrom, the trifurcated main section 14 is conveniently folded onto the continuous main section 12 so that the median flap 20 with its distal end 34 substantially lies parallel to and adjacent the distal end 32 of the continuous main section 12. With this folding operation accomplished, the drape 10 of the invention is ready for use.

Figure 3:
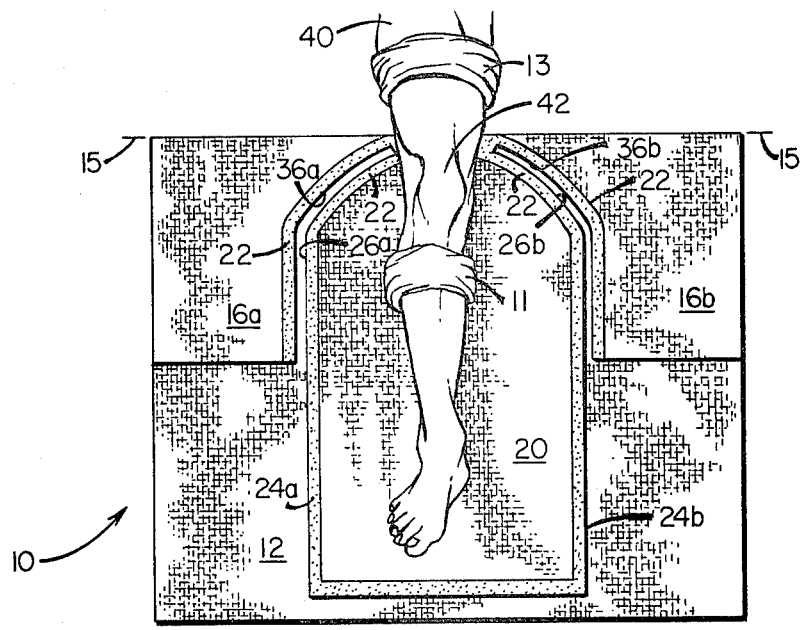
FIG. 3 shows the surgical drape of FIG. 2 positioned under the leg of a patient ready for application.

The median flap 20 comprises essentially the free leg drape portion of the surgical drape 10 of the invention. This is the substantially free part that can envelop the limb, either a leg or a hip of a patient since it has been cut and designed to be essentially free when positioned under the limb of the patient, as shown in FIG. 3, so as to completely envelop the same except for the site of the surgical incision. As may be noted in FIG. 3, a patient's leg 40 has been previously wrapped with a pair of towels 11 and 13 which may be the same towels shown in FIG. 1 and having been cut from the same sheet of material when cutting and forming the surgical drape 10 of the invention. As will be noted, one towel 11 is wrapped below the knee 42 while the other towel 13 is wrapped above the knee. In this particular case, as is evident, knee surgery is contemplated. In such surgery, it is necessary, or at least highly desirable, to completely envelop the limb, except for the surgical site. This is conveniently accomplished by the surgical drape 10 of the invention by positioning it under the limb in such a way that the limb is in substantially the center and almost extends along the length of the median flap 20, and with the narrow connecting junction 28 positioned adjacent the upper edge of the operative site as defined by the lower edge of towel 13, substantially as shown. Any release tape provided on the strip of surgical adhesive 22 may now be removed not only from this narrow connection conjunction 28 but from all areas covering the strip 22.

Figure 4:
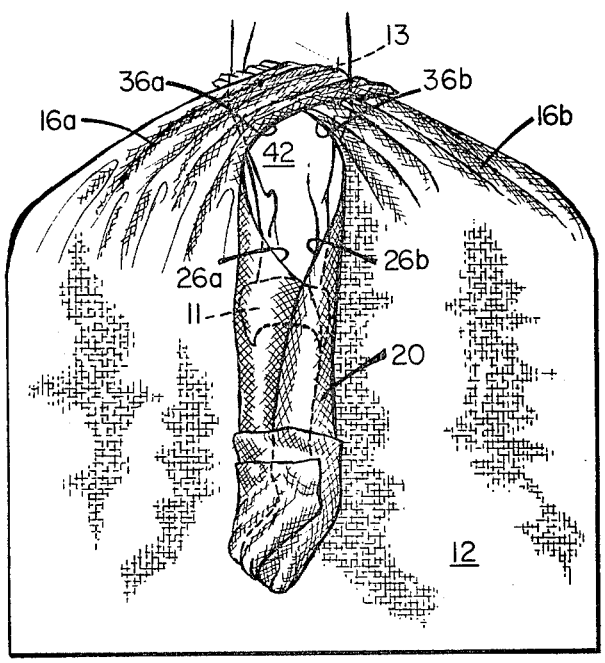
FIG. 4 is a view similar to FIG. 3 but showing the limb of the patient now completely enveloped by the free leg portion and the side flaps of the surgical drape of the invention so as to leave only the operative site, herein a knee, exposed with all other parts of the limb being completely covered thereby.

The surgical drape thus in position under the limb of the patient and with the release tape removed from the strip 22 of surgical adhesive, the upper end of the median flap 20, i.e. the free leg drape portion, is now secured to the limb at its connecting junction 28 underneath and adjacent the edge of the operative site, followed by wrapping the median flap about the limb, with the bottom tucked in, substantially as shown in FIG. 4. This is followed by folding the left side flap 16a above the knee 42, followed by crossing the right side flap 16b over the already folded side flap 16a, so as to completely envelop and seal off the limb in a one-step operation and leaving only the operative site, herein the knee 42, exposed. As may be particularly noted in FIG. 4, the exposed operative site shown by the knee 42 is surrounded at the lower part thereof by the arcuate cuts 26a and 26b of the median flap 20, while its upper periphery is provided by the arcuate segments 36a and 36b of the side flaps 16a and 16b respectively.

Thus, in a one-step application, the surgical drape 10 of the invention has been instrumental in providing a substantially complete seal around the operative site, herein a knee 42. Consequently, undue contamination of exposed surfaces has been avoided. There is also no need for using any other surgical drape, such as a stockinette, in combination with the drape 10 of the invention, which has heretofore been necessary so as to completely cover the limb of the patient except for the operative site. The median flap 20, together with its side flaps 16a and 16b, has already accomplished this. Also there is no need for towel clips to secure the surgical drape 10 of the invention to the limb of the patient for the duration of the operation. Furthermore, due to its being cut from a two-ply sheet as shown and described with reference to FIG. 1, there is less material needed for the surgical drape 10 of the invention, meaning less cost, and also resulting in a much simpler application thereof to a limb preparatory to surgery.

If a hip operation rather than a knee operation is required, then the narrow junction 28 of the folded surgical drape of the invention as shown in FIG. 2 is first applied, with the leg of the patient abducted, to the inner thigh groin area. Thereafter the lower leg is wrapped in the envelope provided by the median flap 20, i.e. the free leg drape portion substantially as shown in FIGS. 3 and 4, and the side flaps 16a and 16b are crossed over one another so as to completely surround the operative site of the hip.

It is thus apparent that there has been provided in accordance with the present invention an improved surgical drape that satisfies the objects and advantages set forth above. While the invention has been described in conjunction with a specific embodiment thereof, it is evident that many alternatives, modifications and variations will be apparent to those skilled in the art in light of the foregoing detailed description. Accordingly, it is intended to embrace all such alternatives, modifications and variations which fall within the spirit and scope of the appended claims.

What is claimed is:

1. Surgical drape for use in hip or knee surgery that provides a substantially complete seal around the operative site in a one step application in which said drape has a substantially rectangular shape and is cut from a sheet made from a two-ply bonded fiber nonabsorbent material, said drape comprising:
    (a) two main sections integrally connected along a main folding line;
    (b) one main section being continuous along said main folding line;
    (c) a second main section being trifurcated into a median flap and a pair of side flaps, with said median flap being connected to said main folding line along a narrow junction covered by a strip of surgical adhesive and said pair of side flaps along wide junctions;
    (d) said median flap being provided about its periphery with a strip of surgical adhesive and said pair of said flaps are each provided with a strip of surgical adhesive about their edges adjacent said median flap;
    (e) said trifurcated main section being folded onto said first main section in such a way that each of said strips of surgical adhesive faces away from said first main section;
    (f) said median flap extending substantially equidistantly from said main folding line as said continuous main section extends therefrom in the opposite direction; and
    (g) said pair of side flaps extending from said main folding line about midway of said median flap.

2. The surgical drape of claim 1 in which said median flap is formed with a pair of arcuate shoulders adjacent its said narrow connecting junction.

3. The surgical drape of claim 1 in which said pair of side flaps are each formed with an arcuate segment commencing from said narrow junction.

4. The surgical drape of claim 1 wherein said median flap is positioned under a limb so that its said narrow connecting junction is adjacent an edge of the operative site.

5. The surgical drape of claim 4 wherein said median flap is wrapped about said limb adjacent one edge of said operative site and said pair of side flaps are wrapped about said limb adjacent a second edge of said operative site so as to combine to provide a substantially complete seal around said operative site.

* * * * *